US005916169A

United States Patent [19]

Hanafy et al.

[11] Patent Number: 5,916,169

[45] Date of Patent: Jun. 29, 1999

[54] PHASED ARRAY TRANSDUCER DESIGN AND METHOD FOR MANUFACTURE THEREOF

[75] Inventors: Amin M. Hanafy, Los Altos Hills; Vaughn R. Marian, Saratoga; Jay Sterling Plugge, Sunnyvale, all of Calif.

[73] Assignee: Acuson Corporation, Mountain View, Calif.

[21] Appl. No.: 08/901,030

[22] Filed: Jul. 25, 1997

Related U.S. Application Data

[63] Continuation of application No. 08/480,677, Jun. 7, 1995, Pat. No. 5,651,365.

[51] Int. Cl.[6] .......... A61B 8/00

[52] U.S. Cl. .......... 600/459; 600/443

[58] Field of Search .......... 600/443, 459, 600/445, 461; 73/626; 367/153

[56] References Cited

U.S. PATENT DOCUMENTS

| | | | |
|---|---|---|---|
| 4,550,607 | 11/1985 | Maslak et al. | 73/626 |
| 5,083,568 | 1/1992 | Shimazaki et al. | 600/459 |
| 5,091,893 | 2/1992 | Smith et al. | 367/153 |
| 5,099,459 | 3/1992 | Smith | 367/153 |
| 5,115,810 | 5/1992 | Watanabe . | |
| 5,396,143 | 3/1995 | Seyed-Bolorforosh et al. | 600/459 |
| 5,492,134 | 2/1996 | Souquet . | |
| 5,546,946 | 8/1996 | Souquet | 600/459 |

*Primary Examiner*—Marvin M. Lateef
*Assistant Examiner*—Maulin Patel
*Attorney, Agent, or Firm*—Brinks Hofer Gilson & Lione

[57] ABSTRACT

A phased array transducer and method for the manufacture thereof having a design that allows the array to focus in a near field of interest and a far field of interest. The array includes a plurality of even and odd numbered transducer elements where the even and odd numbered elements have an active region of particular widths. The width of the active region of the odd numbered elements is different than the width of the active region of the even numbered elements so that the odd numbered elements can be used to image in one field of interest while the even numbered elements can be used to image in another field of interest.

20 Claims, 8 Drawing Sheets

(PRIOR ART) 10

PHASED ARRAY TRANSDUCER DESIGN AND METHOD FOR MANUFACTURE THEREOF

CROSS REFERENCE TO RELATED APPLICATION

This application is a continuation of applicant's copending application, Ser. No. 08/480,677, filed Jun. 7, 1995, which application issued as U.S. Pat. No. 5,651,365 on Jul. 29, 1997.

FIELD OF THE INVENTION

This invention relates to transducers and more particularly to phased array transducers for use particularly in the medical diagnostic field.

Ultrasound machines are often used for observing organs in the human body. Typically, these machines contain transducer arrays for converting electrical signals into pressure waves and vice versa. Generally, the transducer array is in the form of a hand-held probe which may be adjusted in position to direct the ultrasound beam to the region of interest.

FIG. 1 illustrates a prior art transducer array 10 for generating an ultrasound beam. Typically, such an array may have 128 transducer elements 12 in the azimuthal direction. Adapted from radar terminology, the x, y, and z directions are referred to as the azimuthal, elevation, and range directions, respectively.

Each transducer element 12, typically rectangular in cross-section, may comprise a first electrode 14, a second electrode 16 and a piezoelectric layer 18. In addition, one or more acoustic matching layers 20 may be disposed over the piezoelectric layer 18 to increase the efficiency of the sound energy transfer to the external medium. The electrode 14 for a given transducer element 12 may be part of a flexible circuit 15 for providing the hot wire or excitation signal to the piezoelectric layer 18. Electrode 16 for a given transducer element may be connected to a ground shield return 17. To further increase performance, the piezoelectric layer 18 may be plated or metalized on its top and bottom surfaces and the matching layer 20 may also be plated or metalized on all surfaces so that electrode 16 which is in physical contact with the matching layer 20 is electrically coupled to a surface of the piezoelectric layer 18 by the plating as shown in FIG. 1A.

The transducer elements 12 are disposed on a backing block 24. The backing block 24 may be highly attenuative such that ultrasound energy radiated in its direction (i.e., away from an object 32 of interest) is substantially absorbed. In addition, a mechanical lens 26 may be placed on the matching layer 20 to help confine the generated beam in the elevation-range plane and focus the ultrasound energy to a clinically useful depth in the body. The transducer array 10 may be placed in a nose piece 34 which houses the array. Examples of prior art transducer structures are disclosed in Charles S. DeSilets, *Transducer Arrays Suitable for Acoustic Imaging*, Ph.D. Thesis, Stanford University (1978) and Alan R. Selfridge, *Design and Fabrication of Ultrasonic Transducers and Transducer Arrays*, Ph.D. Thesis, Stanford University (1982).

Individual elements 12 can be electrically excited by electrodes 14 and 16, with different amplitude and phase characteristics to steer and focus the ultrasound beam in the azimuthal-range plane. An example of a phased array acoustic imaging system is described in U.S. Pat. No. 4,550,607 issued Nov. 5, 1985 to Maslak et al. and is specifically incorporated herein by reference. U.S. Pat. No. 4,550,607 illustrates circuitry for combining the incoming signals received by the transducer array to produce a focused image on the display screen. When an electrical signal is imposed across the piezoelectric layer 18, the thickness of the layer changes slightly. This property is used to generate sound from electrical energy. Conversely, electrical signals are generated across the electrodes in contact with the piezoelectric layer 18 in response to thickness changes that have been imposed mechanically.

The pressure waves generated by the transducer elements 12 are directed toward an object 32 to be observed, such as the heart of a patient being examined. Each time the pressure wave confronts tissue having different acoustic characteristics, a wave is reflected backward. The array of transducers may then convert the reflected pressure waves into corresponding electrical signals.

For the transducer shown in FIG. 1 the beam is said to be mechanically focused in the elevation direction. The focusing of the beam in the azimuthal direction is done electronically by controlling the timing of the transmissions of each transducer element. This may be accomplished by introducing appropriate phase delays in the firing signals.

Reflected energy from a particular location in the imaging plane is collected by the transducer elements. The resultant electronic signals from individual transducer elements are individually detected and reinforced by introducing appropriate delays. Extensive processing of such data from the entire imaging phase is done to generate an image of the object. Such an image is typically displayed on a CRT monitor.

Generally, higher frequencies of ultrasonic waves are used to improve the resolution of sectional plane images for shallow portions of a human body. Although it may be desirable to image deep in the human body at higher frequencies, these higher frequencies are often absorbed by the object being observed. Therefore, in conventional ultrasound systems, lower frequencies of ultrasonic waves are generally used to improve the resolution of sectional plane images of deeper regions within the human body. Further, typical transducers operating at lower frequencies are generally designed to be wider along the elevation direction in order to provide maximum energy transfer to the far field. Typical transducers operating at higher frequencies are generally designed to be more narrow along the elevation direction in order to improve the resolution of objects observed in the near field. The use of higher frequencies for a transducer designed to operate for the far field (i.e., wider along an elevation direction) will otherwise clutter imaging in the shallow portions of the human body.

It is thus desirable to provide a transducer structure which has optimum performance over a wide range of imaging depths.

It is also desirable to provide a transducer structure capable of switching from an imaging depth in the near field to an imaging depth in the far field and vice versa.

It is desirable to provide a versatile transducer that is capable of discerning structure at relative deep locations within an object without sacrificing near field performance.

SUMMARY OF THE INVENTION

According to a first aspect of the present invention there is provided a transducer array having at least a first transducer element and at least a second transducer element. The first transducer element has an active region of a first width along an elevation direction of the array. The second transducer element has an active region of a second width along the elevation direction of the array. The second width is different from the first width.

According to a second aspect of the present invention there is provided a method of making a transducer for producing an ultrasound beam upon excitation, the transducer being operable to focus in a near field of interest and a far field of interest. The method includes providing a backing block having a top surface, providing an electrode on the top surface of the backing block, providing a layer of piezoelectric material on the electrode, providing a first acoustic matching layer on the piezoelectric layer, the first acoustic matching layer covering about half of the piezoelectric layer in an elevation direction. The first acoustic matching layer has a plated top surface, a plated bottom surface, a plated first edge and a plated second edge. A second acoustic matching layer is provided, the second acoustic matching layer has a plated top surface, a plated bottom surface, a plated first edge and a plated second edge on the piezoelectric layer adjacent to the first acoustic matching layer. The plated second edge of the first matching layer abuts the plated first edge of the second matching layer. A first kerf is diced in an azimuthal direction through the first matching layer and the piezoelectric layer. A second kerf is diced in an azimuthal direction through the second matching layer and the piezoelectric layer. A plurality of kerfs are then diced in an elevation direction through the first matching layer, the second matching layer, the piezoelectric layer and the electrode to form a plurality of transducer elements arranged along the azimuthal direction. The plating from the first edge of the first matching layer and the second edge of the second matching layer is removed for each alternate transducer element. An electrode layer is provided over the first and second acoustic matching layers.

According to a third aspect of the present invention there is provided a method of making a transducer for producing an ultrasound beam upon excitation, the transducer being operable to focus in a near field of interest and a far field of interest. The method includes forming a plurality of first transducer elements arranged in an azimuthal direction, each of the first transducer elements having an active region of a given width in an elevation direction. Forming a plurality of second transducer elements arranged in an azimuthal direction, each of the second transducer elements having an active region of a given width in an elevation direction. The active region of the second transducer elements is smaller than the active region of the first transducer elements. Establishing an electric field through the active region of the first transducer elements to focus in a far field of interest and establishing an electric field through the active region of the second transducer elements to focus in a near field of interest.

According to a fourth aspect of the present invention there is provided a transducer array having a plurality of transducer elements arranged along an azimuthal direction. Each transducer element includes a first electrode, a piezoelectric layer disposed on the first electrode, a first and second acoustic matching layer having a plated top surface, bottom surface and first and second edges. The first and second acoustic matching layer are disposed on the piezoelectric layer adjacent to one another so that the plated second edge of the first acoustic matching layer is in contact with the plated first edge of the second acoustic matching layer. A first kerf extends through the first acoustic matching layer and the piezoelectric layer in an elevation direction. A second kerf extends through the second acoustic matching layer and the piezoelectric layer in an elevation direction. A second electrode is disposed over the first and second acoustic matching layers wherein the second electrode is in contact with the plated top surfaces of the first and second acoustic matching layers. The first and second kerfs define an active region therebetween wherein the second plated edge of the first acoustic matching layer and the first plated edge of the second acoustic matching layer couple the plated top surfaces which are in contact with the second electrode to the plated bottom surfaces which are in contact with the piezoelectric layer. For each even number transducer element along the azimuthal direction, the plated top surfaces of the first and second acoustic matching layers are decoupled from the plated bottom surfaces of the same in an area outside the active region defined by the first and second kerfs.

According to a fifth aspect of the present invention there is provided a method of focusing an ultrasound beam in a field of interest. The method includes providing a plurality of transducer elements arranged along an elevation direction wherein even number elements have an active region of a first width in an elevation direction and odd numbered elements have an active region of a second width in an elevation direction the second width being different from the first width. Exciting the even numbered elements to focus in a first field of interest and exciting the odd numbered elements to focus in a second field of interest different from the first field of interest.

The invention itself, together with further objects and attendant advantages, will best be understood by reference to the following detailed description, taken in conjunction with the accompanying drawings.

DETAILED DESCRIPTION OF THE PRESENTLY PREFERRED EMBODIMENTS

Figure 2:
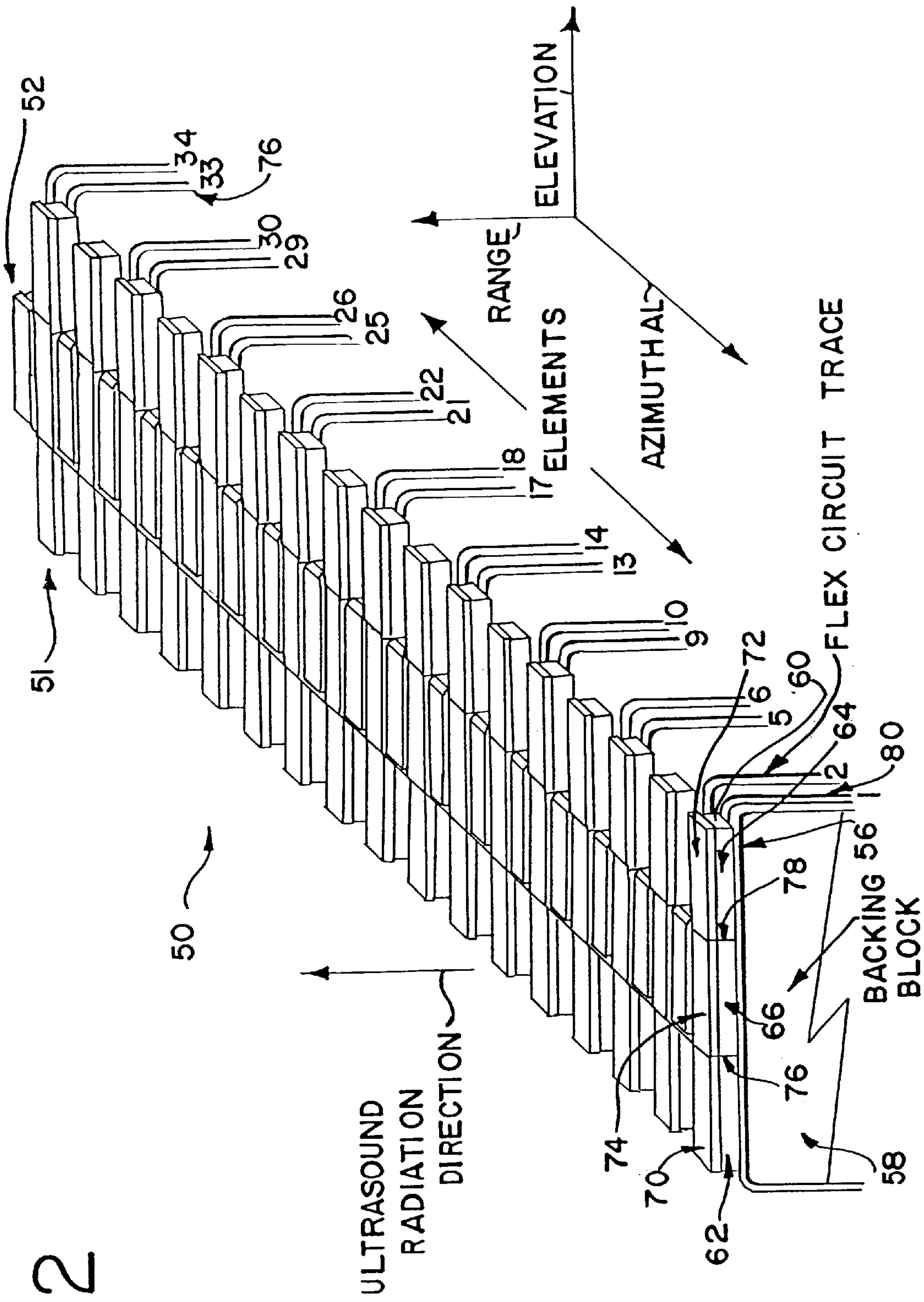
FIG. 2 is a conceptual schematic of a transducer array according to a first preferred embodiment of the present invention.

FIG. 2 is a conceptual schematic of a transducer array 50 according to a first preferred embodiment of the present invention. The transducer array 50 includes a backing block 58, an interconnecting or flexible circuit 56 and a plurality of transducer elements 51 and 52. In a preferred embodiment the backing block 58 is formed of a filled epoxy comprising Dow Corning's part number DER 332 treated with Dow Corning's curing agent DEH 24 and has an Aluminum Oxide filler. The plurality of transducer elements 51 and 52 are arranged along the azimuthal direction and are disposed on the interconnecting circuit or flexible circuit 56. The flexible circuit 56 is disposed on the backing block 58. The flexible circuit 56 may be, for example, any interconnecting design used in the acoustic or integrated circuit fields. The flexible circuit is typically made of a copper layer carrying a lead 80 for exciting the transducer element. The copper layer may be bonded to a piece of polyimide material, typically KAPTON. Preferably the copper layer is coextensive in size with the transducer element. In addition, the interconnect circuit may be gold plated to improve the contact performance. Such a flexible circuit is manufactured by Sheldahl of Northfield, Minn.

The odd numbered elements are formed by transducer elements 51 and the even numbered elements are formed by transducer elements 52. While the even number transducers 52 are shown as having a smaller width in the elevational direction than the odd numbered transducer elements 51 they have in actuality the same physical width as will be explained in greater detail hereinafter with reference to FIG. 6. Preferably, the odd numbered transducer elements 51 are divided into three sections and include a piezoelectric layer 60 having outer piezoelectric portions 62, 64 and a center piezoelectric portion 66. In a preferred embodiment the piezoelectric layer 60 is composed of lead zirconate titanate (PZT). Commercially available PZT such as D3203HD from Motorola Ceramic Products of Albuquerque, New Mexico and PZT-5h from Morgan Matroc, Inc. of Bedford, Ohio are suitable. However, it may be formed of composite material or polymer material PVF. In a preferred embodiment, a matching layer 68 having outer matching layer portions 70, 72 and center matching layer portion 74 is disposed on the piezoelectric portions 62, 64 and 66 respectively. In a preferred embodiment matching layers are made of a filled polymer. The piezoelectric portions 62, 64, 66 and the matching layer portions 70, 72, 74 are separated into three section by kerfs 76 and 78. The kerfs 76 and 78 may extend through the matching layer 68 and substantially through the piezoelectric layer 60. Preferably, a thickness of approximately 50 $\mu$m of the piezoelectric layer 60 is left between the bottom of the kerfs 76 and 78 and the flexible circuit 56. The kerfs 76 and 78 may be formed by a standard dicing blade or a laser, for example, a $CO_2$ laser or excimer laser.

The even numbered transducer elements 52 are illustrated as having only a center portion preferably of substantially the same width as center portion 66 of the odd numbered transducer elements 51. In a preferred embodiment, the even numbered transducer elements 52 have a similar structure as the odd numbered transducer elements 51. Namely, each transducer element 52 includes a piezoelectric layer and a matching layer disposed on the piezoelectric layer. The structure of the even and odd numbered transducer elements 51 and 52 will be described in greater detail with reference to FIGS. 5 and 6.

The flex circuit 56 contains leads or traces 80 which may provide an excitation signal to the respective transducer elements 51 and 52. The leads 80 may, for example, be provided from alternating sides of the transducer elements 51, 52. That is, a pair of transducer elements 51, 52 may receive its excitation signal from leads 80 on one side of the transducer array and the next pair of transducer elements 51,52 may receive its excitation from leads on the other side of the transducer which is not shown for purposes of clarity.

FIG. 2 illustrates conceptually how the transducer array 50 functions. More particularly, the odd numbered transducer elements 51 are shown to have a width in the elevational direction greater than the width of the even numbered transducer elements 52. The width of the transducer element as shown in FIG. 2 represents its active region, i.e., the region of the piezoelectric material which is capable of being excited by the electrodes. Thus for the odd numbered transducer elements 51 the active region includes the center portion 66 and the outer portions 62 and 64 whereas for the even numbered transducer elements 52 the active region includes only the center portion 66.

As was previously discussed, higher frequencies of ultrasonic waves are used to image shallow portions of an object whereas lower frequencies of ultrasonic waves are generally used to image deeper portions of an object. Transducers operating at lower frequencies are generally designed to be wider along the elevation direction in order to provide maximum energy transfer to the far field whereas transducers operating at higher frequencies are generally designed to be narrower along the elevation direction in order to improve the resolution of objects observed in the near field. By providing a transducer array 50 having wide odd numbered transducer elements 51 and narrow even numbered transducer elements 52 in the elevation direction, the transducer array 50 is capable of providing clearer images in both the near and far fields. More particularly, the odd numbered elements 51 are used to image deep within the structure while the even numbered elements 52 are used to image in the near field. The even numbered elements 52 may also be activated along with the odd numbered elements 51 to increase the total energy emitted from the transducer array 50. Switching from activating the even or odd or both transducer elements is performed by the ultrasound system software or microcode, see, for example, U.S. Pat. No. 4,550,607.

Figure 3:
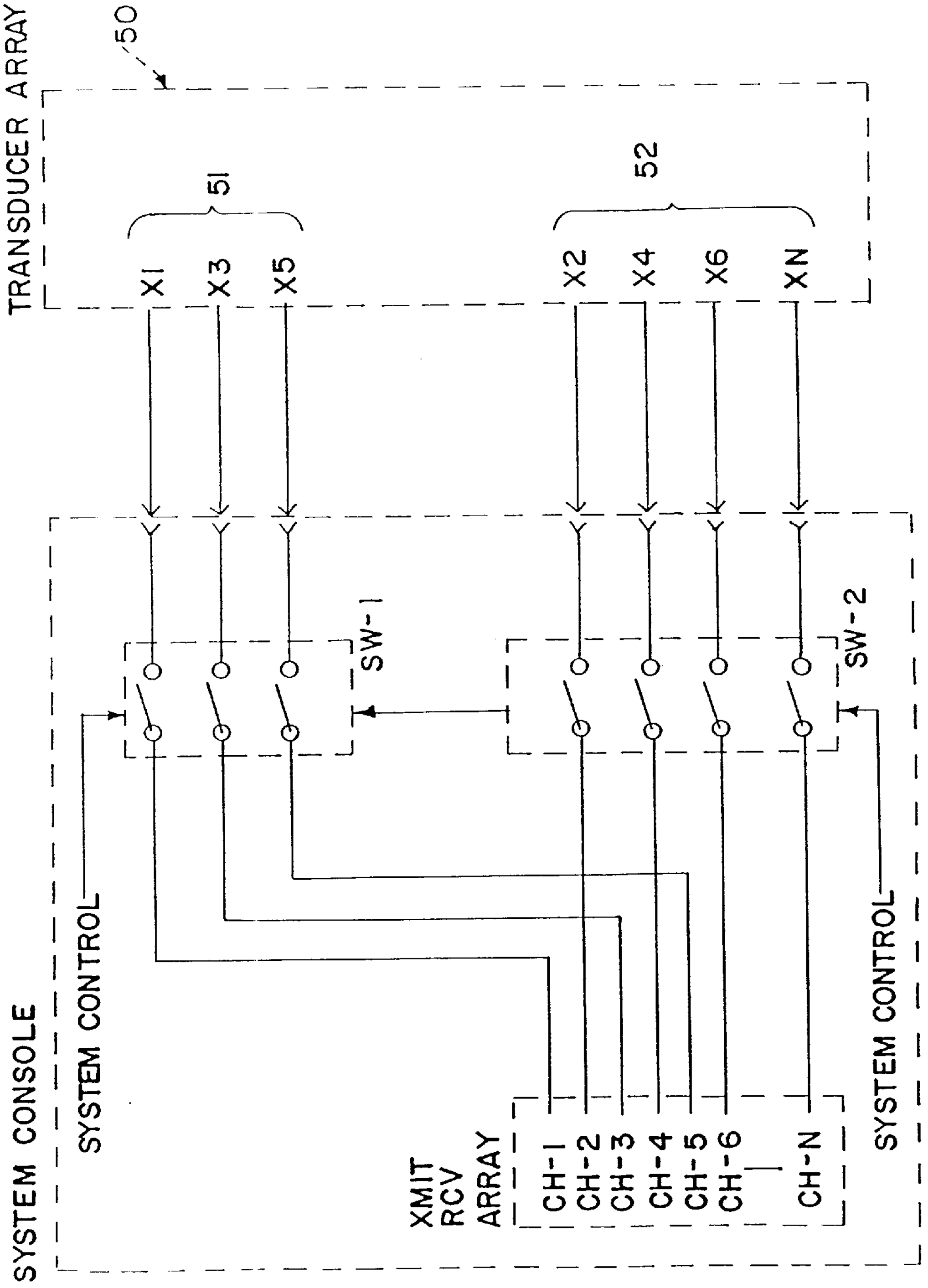
FIG. 3 illustrates a circuit for controlling the excitation of the even and odd numbered transducer elements of the transducer array 50 shown in FIG. 2.

FIG. 3 illustrates a circuit for controlling the excitation of the even and odd numbered elements of the transducer array 50 shown in FIG. 2. The selection of the transducer odd channels for optimum far field performance or the transducer even channels for optimum near field performance is accomplished with high voltage MOS switch arrays SW-1 and SW-2 respectively under the control of the ultrasound machine. The circuitry can be an integral part of the machine or a separate module. The circuit also permits both the odds and evens groups to be used simultaneously for maximum energy transmitted and received.

Figure 4:
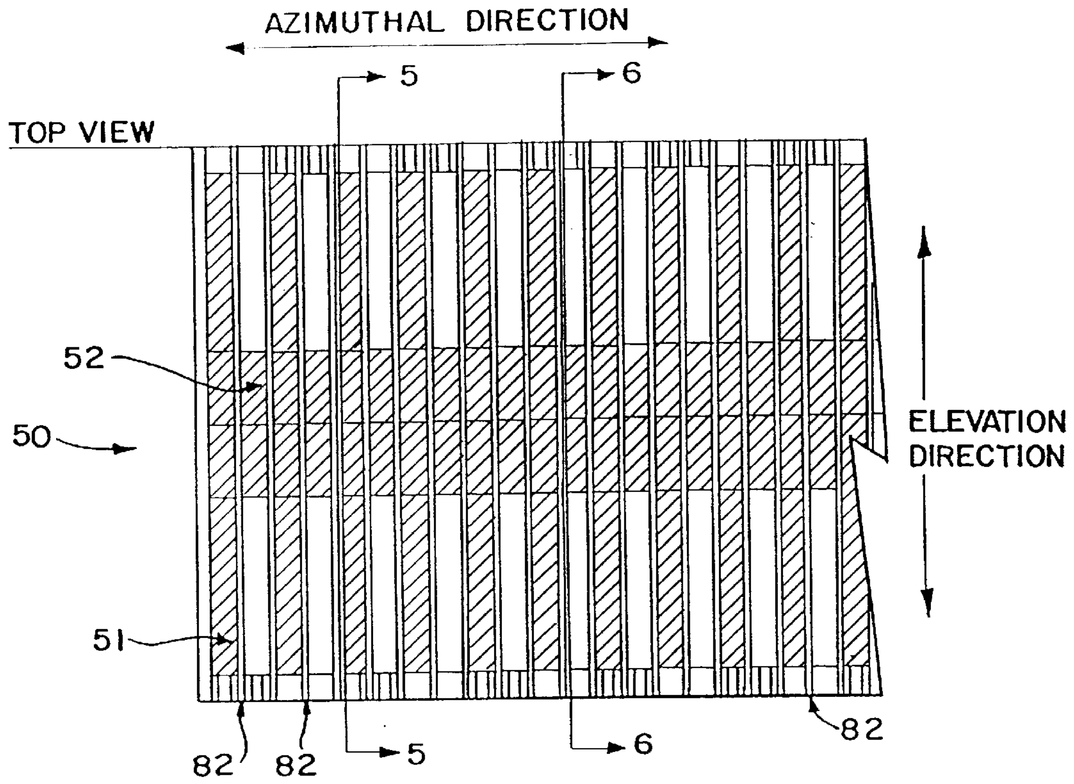
FIG. 4 is a top elevational view of the transducer array shown in FIG. 2.

FIG. 4 illustrates a top view of the transducer array 50 shown in FIG. 2 where the active regions of the even and odd numbered transducer elements 51 and 52 are illustrated by hatched lines. Between each transducer element is a kerf 82 extending in the elevation direction to electrically isolate each transducer element from one another.

Figure 5:
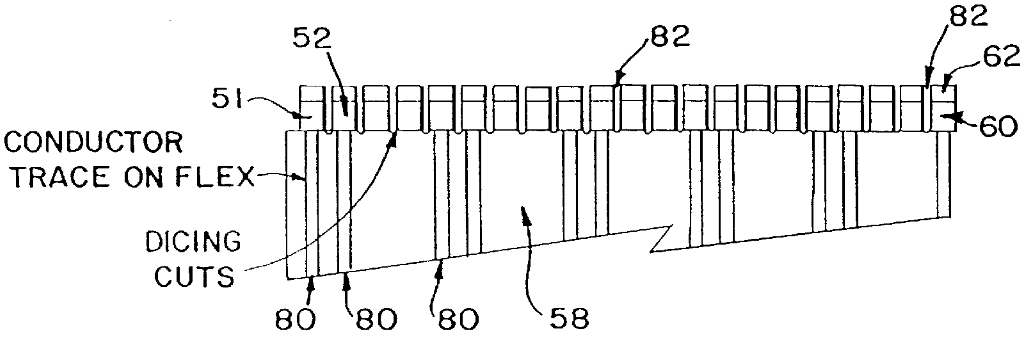
FIG. 5 is a side azimuthal view of the transducer array shown in FIG. 2.

FIG. 5 illustrates a side azimuthal view of the transducer array 50 shown in FIGS. 2 and 4. As previously discussed, the flex circuit contains leads or traces 80 which may provide an excitation signal to the respective transducer elements 51 and 52. The leads 80 may, for example, be provided from alternating sides of the transducer elements 51, 52. That is, a pair of transducer elements 51, 52 may receive its excitation signal from leads 80 on one side of the transducer array and the next pair of transducer elements 51,52 may receive its excitation signal from leads on the other side of the transducer. In addition, kerfs 82 extend along the elevation direction to separate the transducer elements from one another. The kerfs 82 may be formed using a dicing blade or a laser. The kerfs 82 extend through the matching layer 68, piezoelectric layer 60, flexible circuit and into a portion of the backing block 58. The spacing between adjacent transducer elements is preferably half a wavelength.

Figure 6:
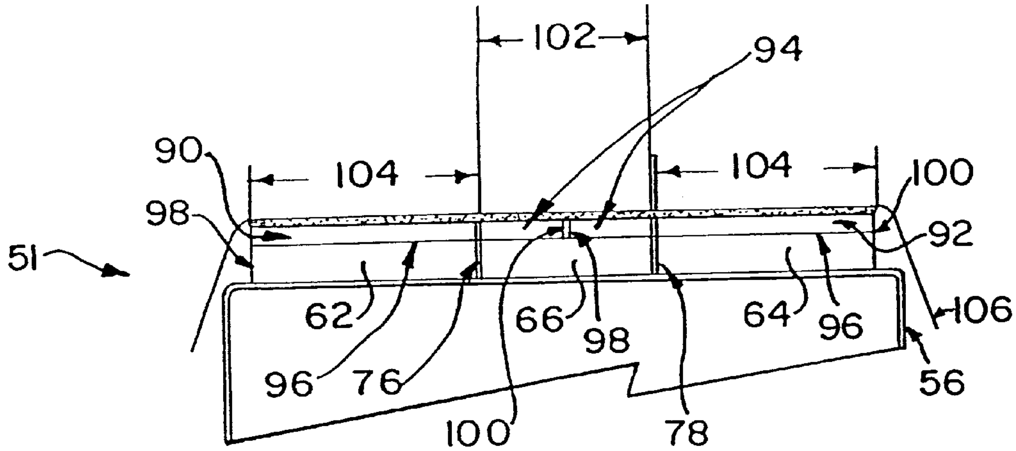
FIG. 6 is a cross-sectional view of the transducer array taken along the lines 5—5 of FIG. 4.

FIG. 6 is a cross-sectional view of the transducer array shown in FIG. 4 taken along line 5—5. FIG. 6 illustrates the cross-section of an odd numbered transducer element 51. Preferably, the odd numbered transducer element 51 is divided into three sections and includes a piezoelectric layer 60 having outer piezoelectric portions 62, 64 and a center piezoelectric portion 66. A first matching layer 90 is disposed over one half of the piezoelectric layer 60 and a second matching layer 92 is disposed over the remaining half of the piezoelectric layer 60 as illustrated. In a preferred embodiment, the first and second matching layers 90 and 92 are plated on all surfaces. More particularly, each matching layer has a plated top surface 94, a plated bottom surface 96, a plated first edge 98 and a plated second edge 100. The second edge 100 of the first matching layer 90 is in contact with the first edge 98 of the second matching layer.

The first kerf 76 extends through the first matching layer 90 and substantially through the piezoelectric layer 60 but not through the flexible circuit 56. The second kerf 78 extends through the second matching layer 92 and substantially through the piezoelectric layer 60 but not through the flexible circuit 56. The two kerfs 76 and 78 divide each transducer element into three sections, namely a center section 102 and outer sections 104.

An electrode or ground flex circuit 106 is then disposed over the first and second matching layers 90 and 92 so that the electrode 106 is in electrical contact with the top plated surfaces 94 of the first and second matching, layers. In the outer sections 104 the electrode 106 makes electrical contact with the top surface of the piezoelectric layer 60 by the plated first or second matching layers 90 and 92. More particularly, in the left outer section 104, electrode 106 is coupled to the top surface of the piezoelectric layer 60 by the plated top surface 94, plated first edge 98 and plated bottom surface 96 of the first matching layer 90. In the right outer section 104, electrode 106 is coupled to the top surface of piezoelectric layer 60 by the plated top surface 94, plated second edge 100 and plated bottom surface 96 of the second matching layer 92. The left and right outer sections 104 are electrically isolated from the center section 102 and from each other by kerfs 76 and 78. Because the kerfs 76 and 78 do not extend through the bottom surface of the piezoelectric layer 60, the flex circuit is in continuous contact with the bottom surface of the piezoelectric layer 60. Thus for the odd numbered transducer elements, the active region is the entire width of the transducer element. Thus the piezoelectric layer in the center and outer portions can be excited by flexible circuit 56 and electrode 106.

Figure 7:
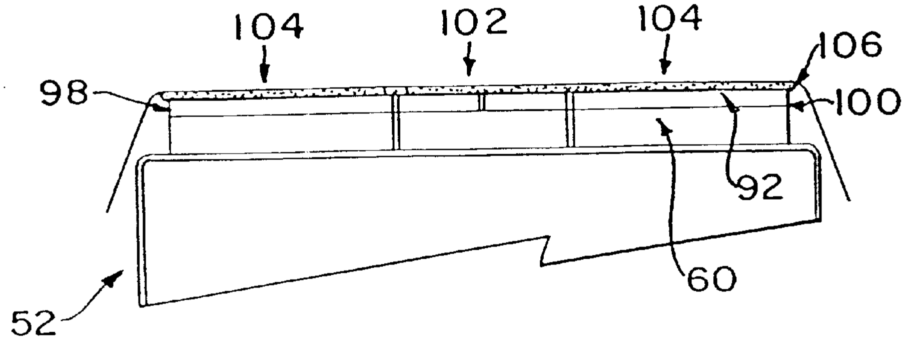
FIG. 7 is a cross-sectional view of the transducer array taken along the lines 6—6 of FIG. 3.

FIG. 7 is a cross-sectional view of the transducer array shown in FIG. 4 taken along line 6—6. FIG. 7 illustrates the cross-section of an even numbered transducer element 52. Preferably, the even numbered transducer elements 52 have the same structure as the odd numbered transducer elements with one exception. The electrical connection between the electrode 106 and the plated first and second matching layers 90 and 92 is severed in the outer sections 104. The electrical connection in the outer sections 104 may be severed by destroying the plating on the first edge 98 of the first matching layer 90 and the second edge 100 of the second matching layer 92. The plating may be destroyed using a dicing saw, a $CO_2$ laser or an excimer laser, for example. Thus the outer sections 104 are inactive for the even numbered transducer elements 52.

The center portion 102 of the even numbered transducer elements 52, however, can still be activated by the flexible circuit 56 and the electrode 106. The connections of electrode 106 and flexible circuit 56 in the center portion 102 of the even numbered transducer elements 52 is the same as already described with reference to the odd numbered transducer elements 51 and thus need not be repeated here. Kerfs 76 and 78 electrically isolate the center portion 102 from the outer portions 104. Thus when center portion 102 is activated in the even numbered transducer elements 52, outer portions 104 remain inactive.

In a preferred embodiment, the width of the active region of the odd numbered transducer elements 51 i.e., its actual width in the elevation direction, is about 7 mm. The width of the active region of the even numbered transducer elements 52 is about 3 mm. Of course these dimensions are given for illustration purposes only and are not meant as limitations. Other dimensions may be used depending upon the particular application of the transducer array. In addition, while the center portion of the even numbered transducer elements 52 is shown as having the same width of the center portion of the odd numbered transducer elements 51, this dimension may be varied also. Also, the terms “odd” and “even” are interchangeable and in another embodiment, the odd numbered transducer element may have a narrow aperture while the even numbered elements may have a wide aperture.

Figure 8B:
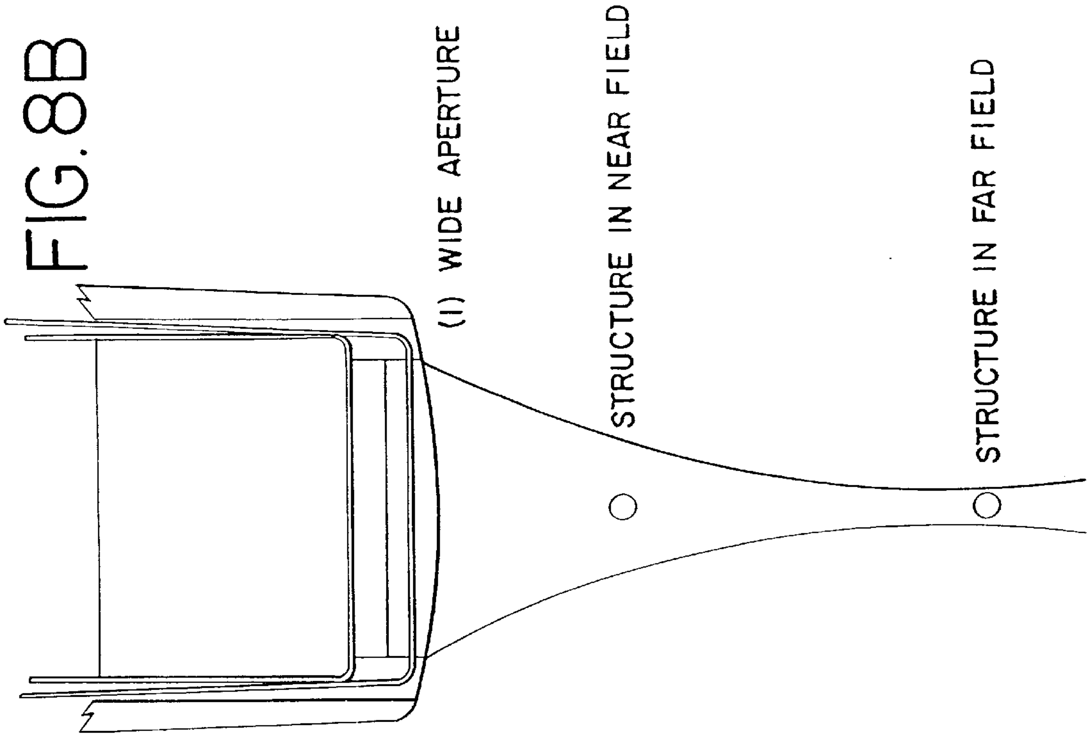
FIGS. 8(*a*) and (*b*) are cross-sectional views of the transducer array showing the exiting beam profile for a narrow and wider transducer element respectively.
Figure 8A:
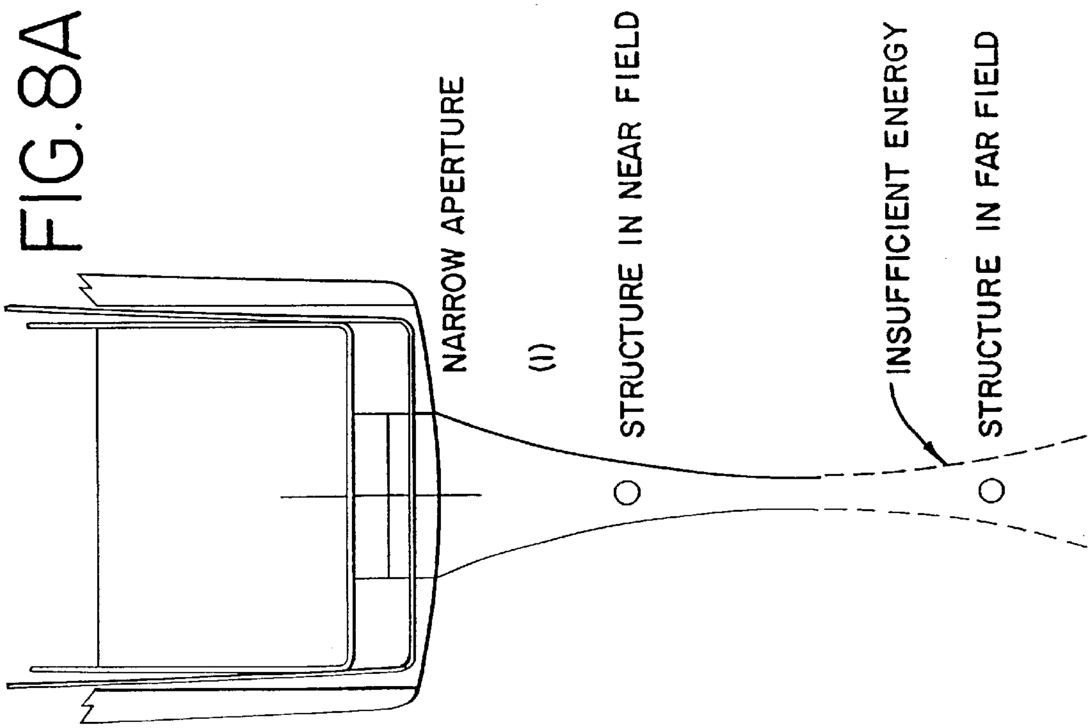

FIG. 8(*a*) is a cross-sectional view illustrating the exiting beam profile for a narrow aperture transducer element. FIG. 8(*b*) is a cross-sectional view illustrating the exiting beam profile for a wide aperture transducer element. To image an object in a near field, the narrow aperture beam is produced by activating only the even numbered transducer segments 52. When the even numbered transducer segments 52 are activated, the beam profile allows clear imaging of objects in the near field, however, there is insufficient energy to image objects in the far field. To image an object in the far field, the odd numbered transducer segments 51 are activated either alone or in combination with the even numbered transducer segments 52. By activating the odd numbered transducer segments 51, a wider beam profile is produced which provides sufficient energy to image in the far field. Preferably the near field ranges from about 0 to 20 mm from the lens of the transducer array and the far field ranges from about 20 mm to 200 mm from the lens.

In a preferred embodiment the transducer array 50 is operated in the 2.5 to 20 MHz frequency range and more preferably in the 5 to 10 MHz frequency range.

Figure 9:
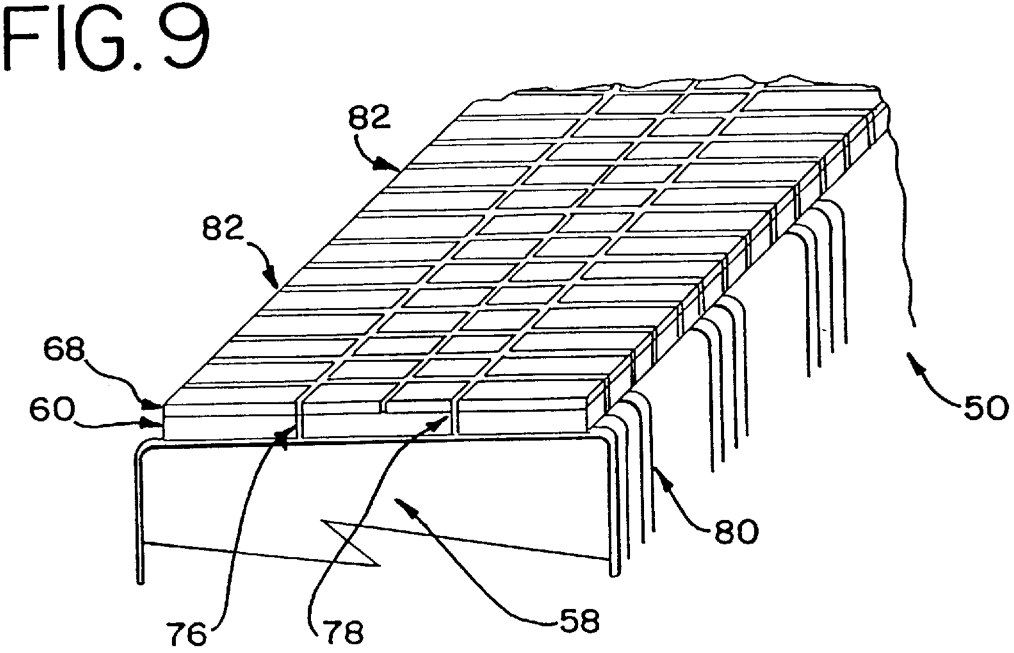
FIG. 9 is a perspective view of a transducer array with the top electrode removed.

FIG. 9 is a schematic of a transducer array with the top or ground electrode removed. It can be seen from FIG. 9 that in actuality the physical width of the even numbered transducer segments 52 is the same as the odd numbered transducer segments 51.

Figure 1A:
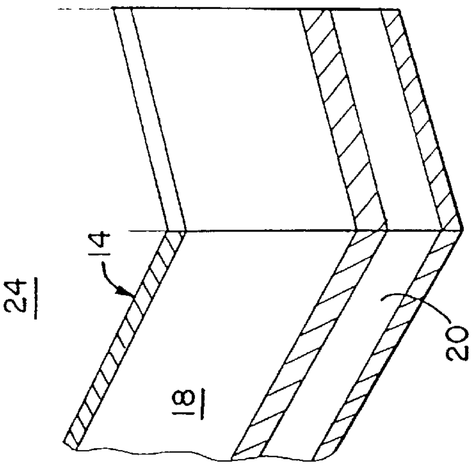
FIG. 1A is an exploded view of a portion of the transducer array shown in FIG. 1.
Figure 1:
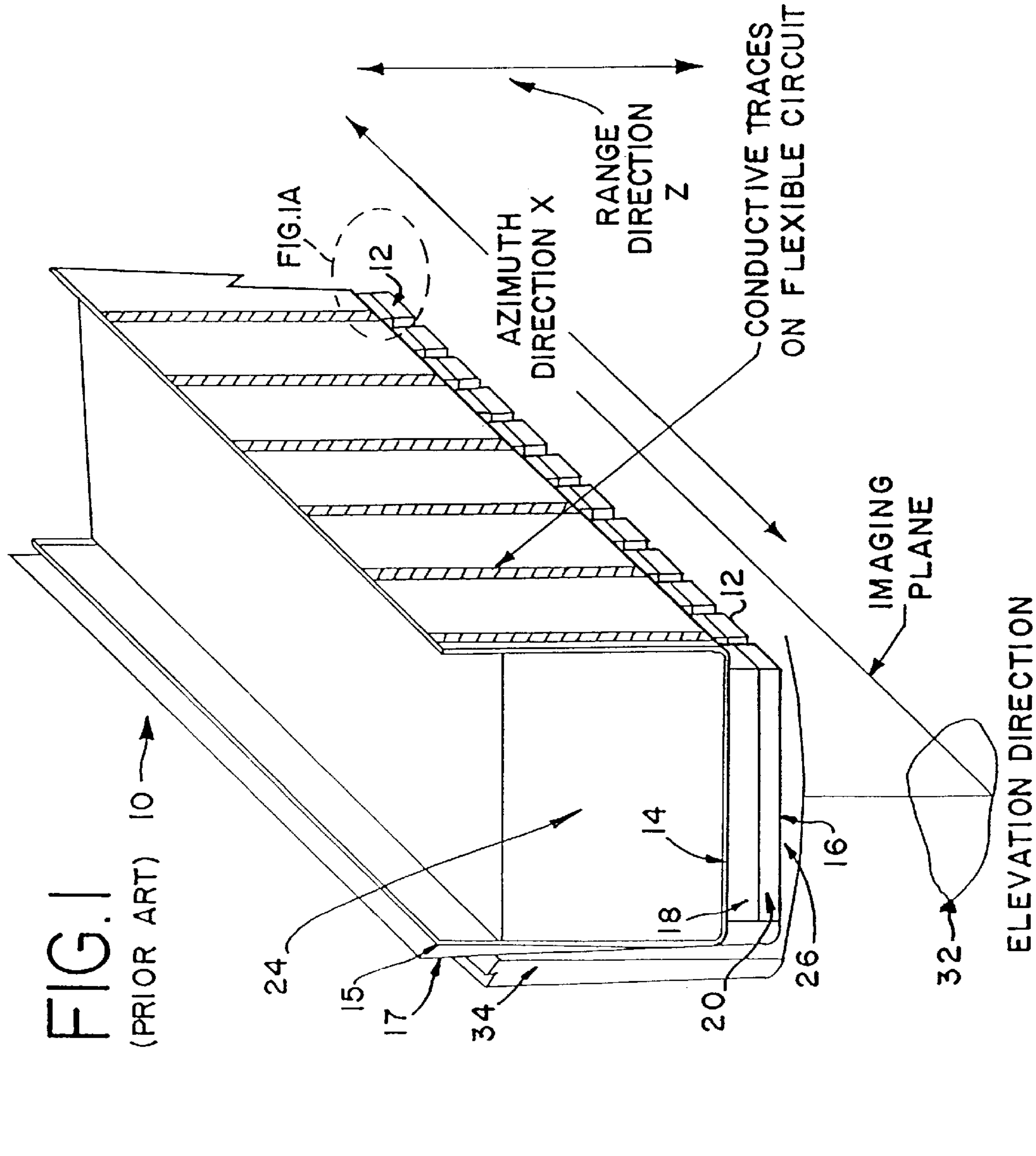
FIG. 1 is a perspective view of a prior art transducer array.
Figure 10:
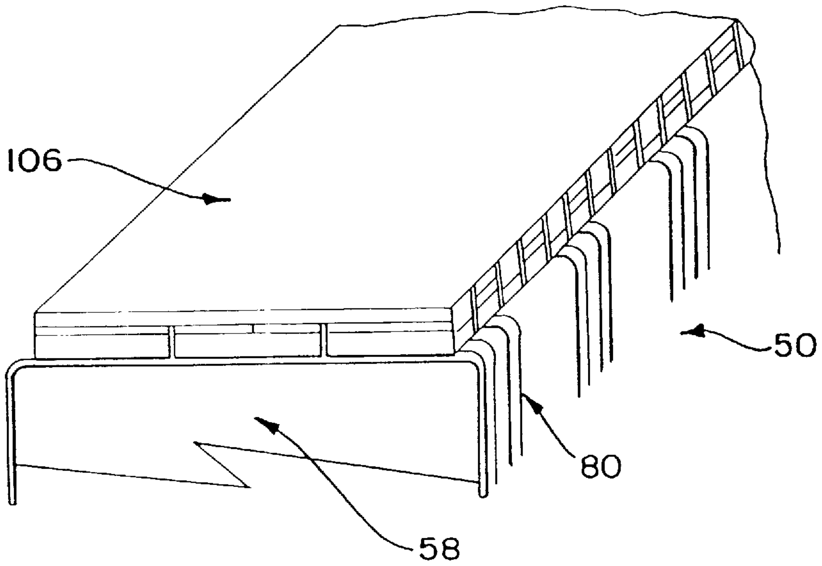
FIG. 10 is a perspective view of the transducer array shown in FIG. 9 with the top electrode disposed over the array.

FIG. 10, is a schematic of the transducer array shown in FIG. 9 with the top or ground electrode 106 disposed over the array 50. Electrode 106 is common to the entire array 50 and may be connected to a ground return shield as shown in FIG. 1

Figure 11:
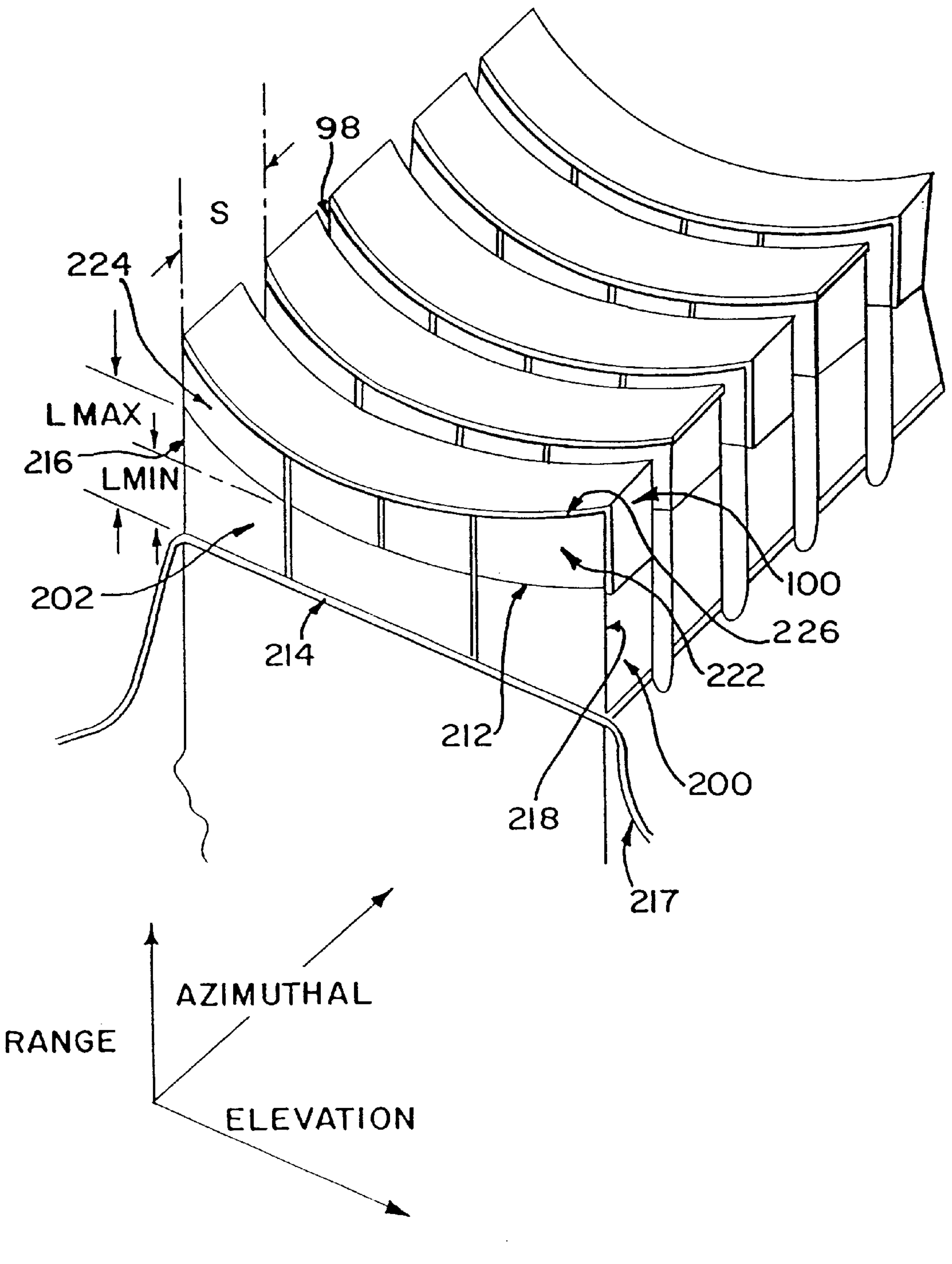
FIG. 11 is a perspective view of a transducer array according to a second preferred embodiment of the present invention.

FIG. 11 is a schematic of a transducer array according to a second preferred embodiment of the present invention. In this preferred embodiment, the transducer elements 200 have a plano-concave shape. In this preferred embodiment the thickness of the piezoelectric layer 202 varies in the elevation direction. U.S. Pat. No. 5,415,175 issued May 16, 1995 to Hanafy et al., which is specifically incorporated herein by reference, discloses transducer elements having such a structure.

More particularly, the transducer elements 25 200 have a front portion 212, a back portion 214, and two sides 216 and 218. The front portion 212 is the surface which is facing the region to be examined. The back portion 214 is generally a planar surface. The front portion 212 is generally a non-planar surface, the thickness of the element 200 being greater at each of the sides 216 and 218 and smaller between the sides. Although the front portion 212 is illustrated as having a continuously curved surface, front portion 212 may include a stepped configuration, a series of linear segments, or any other configuration wherein the thickness of element 200 is greater at each of the sides 216 and 218 and decreases in thickness at the center, resulting in a negatively "curved" front portion 212.

It can be seen that the plated first edge 98 of the first acoustic matching layer and the plated second edge 100 of the second acoustic matching layer are removed for every other transducer element.

Preferably, the element 200 is a plano-concave structure and as already described with reference to the transducer elements 51 and 52 may be composed of the piezoelectric material of lead zirconate titanate (PZT). However, the element 200 may be formed of composite material or polymer material PVF. A flex circuit 217 is utilized to excite one electrode of the respective transducer elements 200. The top or ground electrode of the transducer array is not shown for clarity. Two curved matching layers 222 and 224 are disposed on the front portion 212 of transducer element 200. The matching layers 222 and 224 are preferably made of a filled polymer. Moreover, the thickness of the matching layers 222 and 224 are preferably defined by the equation:

$$LML=(1/2)(LE)(CML/CE),$$

where LML is the thickness of the matching layer at a given thickness of the transducer element LE, CML is the sound speed of the matching layer, and CE is the sound speed of the transducer element. Thus, the curvature of the front portion 212 of the piezoelectric layer 202 may be different than the curvature of the top portion 226 of the matching layers 222 and 224 because the thickness of the matching layer depends on the thickness of the element at the corresponding location. By the addition of matching layers 222 and 224, the fraction bandwidth can be improved further and with increased sensitivity due to matching. However, the thickness difference between the edge and center of the assembled substrates will control the desired bandwidth increase, and the shape of the curvature will control the base bandshape in the frequency domain. Further, because both the transducer element 200 and the matching layers 222 and 224 have a negative curvature, there is additive focusing in the field of interest.

Each element 200 has a maximum thickness LMAX and a minimum or smallest thickness LMIN. Preferably the sides 216 and 218 both are equal to the thickness LMAX and the center of element 200 is at the thickness of LMIN. However, each of the sides 216, 218 do not have to be the same thickness and LMIN does not have to be in the exact center of the transducer element to practice the invention.

The bandwidth increase for a given transducer configuration is approximated by LMAX/LMIN. The bandwidth may be increased just large enough so that there is no need to redesign the already existing hardware for generating the desired frequency activation of the transducer. Typically, this may be an increase in bandwidth of up to 20 percent. Thus, the bandwidth may be increased from zero to 20 percent by increasing the thickness of LMAX relative to LMIN from zero to 20 percent, respectively. For example, if a transducer has an LMAX of 0.012 inches and an LMIN of 0.010 inches, the bandwidth is increased by 20 percent as compared to a transducer having a uniform thickness of 0.010 inches. Preferably, a minor thickness variation of 10 to 20 percent should be utilized. This results in the maximum bandwidth increase, approximately 10 to 20 percent, respectively, without the need to change any of the existing hardware.

In order to receive the full benefit of the invention, that is, increasing the bandwidth greater than 20 percent, it may be necessary to redesign the hardware for exciting the transducer at such a broad range of frequencies. As seen by the above equation, the greater the thickness variation, the greater the bandwidth increase. Bandwidth increases of up to 300 percent for a given design may be achieved in accordance with the principles of the invention. Thus, the thickness LMAX would be approximately three times greater than the thickness LMIN. The bandwidth of a single transducer element, for example, may range from 2 Megahertz to 11 Megahertz, although even greater ranges may be achieved in accordance with the principles of this invention. Because the transducer array constructed in accordance with this invention is capable of operating at such a broad range of frequencies, contrast harmonic imaging may be employed with a single transducer array for observing both the fundamental and second harmonic.

Therefore, by controlling the curvature shape of the transducer element (i.e. cylindrical, parabolic, gaussian, stepped, or even triangular), one can effectively control the frequency content of the radiated energy. In addition, because the signal in the center of the transducer is stronger than at the ends or sides 216 and 218, correct apodization occurs. This is due to the fact that the electric field between the two electrodes on the front portion 212 and bottom portion 214 is greatest at the center of the transducer element 200, reducing side lobe generation.

Further, because the transducer array constructed in accordance with the present invention is capable of operating at a broad range of frequencies, the transducer is capable of receiving signals at center frequencies other than the transmitted center frequency.

It is to be understood that the forms of the invention described herewith are to be taken as preferred examples and that various changes in the shape, size and arrangement of parts may be resorted to, without departing from the spirit of the invention or scope of the claims.

What is claimed is:

1. A transducer array comprising:

at least a first transducer element, said first transducer element having an active region of a first width along an elevation direction of said array; and at least a second transducer element sequentially disposed adjacent to the first transducer element, said second transducer element having an active region of a second width along said elevation direction of said array, said second width being different from said first width.

2. A transducer array according to claim 1 wherein said at least first and second transducer elements are arranged along an azimuthal direction.

3. A transducer array according to claim 1 wherein said at least first transducer element provides focusing in a near field of interest and said at least second transducer element provides focusing in a far field of interest.

4. A transducer array according to claim 1 further comprising a plurality of first and second transducer elements arranged along said azimuthal direction.

5. A transducer array according to claim 4 wherein said first transducer elements alternate with said second transducer elements along said azimuthal direction.

6. A transducer array according to claim 1 wherein said active region of said first transducer element is smaller than said active region of said second transducer element.

7. A transducer array according to claim 1 wherein said active region of said first transducer is in the center of said first transducer and said active region of said second transducer extends the entire width of said second transducer.

8. A method of making a transducer for producing an ultrasound beam upon excitation, said transducer being operable to focus in a near field of interest and a far field of interest, said method comprising the steps of:

providing a backing block having a top surface;

providing an electrode on said top surface of said backing block;

providing a layer of piezoelectric material on said electrode;

providing a first acoustic matching layer on said piezoelectric layer, said first acoustic matching layer covering about half of said piezoelectric layer in an elevation direction, said first acoustic matching layer having a plated top surface, a plated bottom surface, a plated first edge and a plated second edge;

providing a second acoustic matching layer having a plated top surface, a plated bottom surface, a plated first edge and a plated second edge on said piezoelectric layer adjacent to said first acoustic matching layer wherein, said plated second edge of said first matching layer abuts said plated first edge of said second matching layer;

dicing a first kerf in an azimuthal direction through said first matching layer and said piezoelectric layer;

dicing a second kerf in an azimuthal direction through said second matching layer and said piezoelectric layer;

dicing a plurality of kerfs in an elevation direction through said first matching layer, said second matching layer, said piezoelectric layer and said electrode to form a plurality of transducer elements arranged along said azimuthal direction;

removing said plating from said first side of said first matching layer and said second side of said second matching layer for each alternate transducer element; and providing an electrode layer over said first and second acoustic matching layers.

9. A method of making a transducer for producing an ultrasound beam upon excitation, said transducer being capable of focusing in a near field of interest and a far field of interest, said method comprising the steps of:

forming a plurality of first transducer elements arranged in an azimuthal direction, each of said first transducer elements having an active region of a given width in an elevation direction;

forming a plurality of second transducer elements arranged in an azimuthal direction, each of said second transducer elements having an active region of a given width in an elevation direction, said active region of said second transducer elements being smaller than the active region of said first transducer elements;

establishing an electric field through said active region of said first transducer elements to focus in a far field of interest; and establishing an electric field through said active region of said second transducer elements to focus in a near field of interest.

10. A transducer array comprising a plurality of transducer elements arranged along an azimuthal direction each transducer element comprising:

a first electrode;

a piezoelectric layer disposed on said first electrode;

a first acoustic matching layer having a plated top surface, bottom surface and first and second edges, said first acoustic matching layer being disposed on said piezoelectric layer;

a second acoustic matching layer having a plated top surface, bottom surface and first and second edges, said second acoustic matching layer disposed on said piezoelectric layer adjacent to said first acoustic matching layer wherein said plated second edge of said first acoustic matching layer is in contact with said plated first edge of said second acoustic matching layer;

a first kerf extending through said first acoustic matching layer and said piezoelectric layer in an elevation direction;

a second kerf extending through said second acoustic matching layer and said piezoelectric layer in an elevation direction;

a second electrode disposed over said first and second acoustic matching layers wherein said second electrode is in contact with said plated top surfaces of said first and second acoustic matching layers wherein said first and second kerfs define an active region therebetween wherein said second plated edge of said first acoustic matching layer and said first plated edge of said second acoustic matching layer couples said plated top surfaces which are in contact with said second electrode to said bottom surfaces which are in contact with said piezoelectric layer;

wherein for each even number transducer element along said azimuthal direction said plated top surfaces of said first and second acoustic matching layers are decoupled from said bottom surfaces of the same in an area outside said active region defined by said first and second kerfs.

11. A transducer array according to claim 10 wherein said first edge of said first acoustic matching layer and said second edge of said second acoustic matching layer are severed to decouple said plated top surfaces of said first and second acoustic matching layers from said bottom surfaces.

12. A transducer array according to claim 10 wherein said active region defined by said first and second kerfs is in the center of said transducer array along said elevation direction.

13. A method of focusing an ultrasound beam in a field of interest comprising the steps of:

providing a plurality of transducer elements arranged along an elevation direction wherein even number elements have an active region of a first width in an elevation direction and odd numbered elements have an active region of a second width in an elevation direction said second width being different from said first width;

exciting said even numbered elements to focus in a first field of interest; and exciting said odd numbered elements to focus in a second field of interest different from said first field of interest.

14. A method according to claim 13 wherein said first width is smaller than said second width so that when said even numbered elements are excited said ultrasound beam is focused in a near field of interest and when said odd numbered elements are excited said ultrasound beam is focused in a far field of interest.

15. A transducer array according to claim 1 wherein said first and said second transducer elements each have a surface region facing a region of examination that is non-planar.

16. A transducer array according to claim 15 wherein said non-planar surface is curved.

17. A transducer array according to claim 15 wherein said non-planar surface is plano-concave.

18. A transducer array according to claim 1 wherein the first and second transducer elements each include a piezoelectric layer comprising a thickness at a first point on a surface facing a region of examination less than a thickness at a second point on the surface, the surface being generally non-planar.

19. A transducer array according to claim 18 wherein said piezoelectric layer has side portions at each end of said piezoelectric layer wherein the thickness of the piezoelectric layer is at a maximum near said side portions and at a minimum substantially near a center of said piezoelectric layer.

20. A transducer according to claim 19 further comprising an acoustic matching layer positioned between an object to be examined and at least one of said elements.

* * * * *

UNITED STATES PATENT AND TRADEMARK OFFICE

CERTIFICATE OF CORRECTION

PATENT NO. : 5,916,169

DATED : June 29, 1999

INVENTOR(S) : Amin M. Hanafy et al.

It is certified that error appears in the above-indentified patent and that said Letters Patent is hereby corrected as shown below:

In column 4, line 51, change "3" to --4--.

In column 5, line 35, change "5h" to --5H--.

In column 7, line 36, after "matching" delete "," (comma).

In column 8, line 59, after "10" delete "," (comma).

In column 8, line 63, after "1" insert --.-- (period).

In column 9, line 6, after "elements" delete "25".

Signed and Sealed this

Eighteenth Day of April, 2000

Attest:

Q. TODD DICKINSON

Attesting Officer

*Director of Patents and Trademarks*